United States Patent [19]

Zupanick et al.

[11] Patent Number: 4,671,662
[45] Date of Patent: Jun. 9, 1987

[54] LUMINESCENSE AND REFLECTANCE DETECTION RADIOMETER WITH CHANGEABLE OPTICAL ASSEMBLY

[75] Inventors: Joseph E. Zupanick, Richardson; Carl D. McBride, Garland, both of Tex.

[73] Assignee: Atlantic Richfield Company, Los Angeles, Calif.

[21] Appl. No.: 746,050

[22] Filed: Jun. 18, 1985

[51] Int. Cl.[4] ............................................. G01N 21/64
[52] U.S. Cl. .................................. 356/417; 250/458.1; 356/419
[58] Field of Search ................ 250/253, 339, 349, 353, 250/372, 458.1, 459.1, 461.1; 356/221, 222, 224, 225, 317, 416, 417, 419

[56] References Cited

U.S. PATENT DOCUMENTS

| | | | |
|---|---|---|---|
| 3,598,994 | 8/1971 | Markle | 356/317 |
| 3,641,344 | 2/1972 | Markle | 250/459.1 |
| 3,769,516 | 10/1973 | Markle et al. | 356/323 |
| 3,864,037 | 2/1975 | Johnson | 356/418 |
| 4,236,071 | 11/1980 | Chimenti | 250/253 |
| 4,301,372 | 11/1981 | Giering et al. | 356/317 |
| 4,336,459 | 6/1982 | Fay | 250/461.1 |
| 4,433,245 | 2/1984 | Poultney | 250/458.1 |
| 4,478,513 | 10/1984 | Skinner et al. | 350/172 |
| 4,586,786 | 5/1986 | Suzuki et al. | 350/172 |

OTHER PUBLICATIONS

Oriel Corporation Precision Motorized Positioner Brochure Jul. 10, 1981.
Hemphill et al., Proc. 6th International Symp on Remote Sensing of Environment, Ann Arbor, Mich. (13-16 Oct. 1969).

Primary Examiner—F. L. Evans
Attorney, Agent, or Firm—F. Lindsey Scott; Drude Faulconer

[57] ABSTRACT

The present invention provides a radiometer for simultaneously detecting luminescence and reflectance about a particular Fraunhofer line from a material (i.e. target) which includes an interchangeable optical filter assembly of lightweight construction for each Fraunhofer line of interest which substantially alleviates the adverse polarization effects normally experienced in radiometers of this type and which further provides an improved balance between the two light beams being sensed by the radiometer. The optical filter assembly includes a single beamsplitter which reflects the majority of the light from the target with little adverse polarization effects to a narrow band filter which passes only the light existing at the particular Fraunhofer line (i.e. "c" component of luminescence). The remaining smaller fraction of the light passes through the beamsplitter with only slightly greater polarization to a broad band filter which, in turn, passes only the light in the continuums adjacent the Fraunhofer line (i.e. "d" component of luminescence). The intensity of the light from the narrow and broad band filters are measured for use in calculating the luminescence and reflectance emanating from the target.

20 Claims, 10 Drawing Figures

LUMINESCENSE AND REFLECTANCE DETECTION RADIOMETER WITH CHANGEABLE OPTICAL ASSEMBLY

DESCRIPTION

1. Technical Field

The present invention relates to a means for detecting and measuring luminescense and reflectance of a target material in the presence of direct sunlight and more particularly relates to a radiometer for measuring luminescense and reflectance of a target material on site having an interchangeable optical assembly for measuring luminescense at selected particular Fraunhofer absorption lines which allows the radiometer to be of lightweight and field portable construction.

2. Background Art

Fraunhofer line dicriminator systems are well known for sensing, measuring, and recording luminescence which is radiated from certain materials when stimulated by the sun. These systems operate on the known principle that sunlight contains identical Fraunhofer absorption lines before and after it is reflected from a material. In contrast, however, luminescence energy radiated from that material is broad band and contains no Fraunhofer absorption lines. Thus, luminescence produced by reflected sunlight can be sensed and measured by comparing the light level or intensity within a selected Fraunhofer absorption line to the light intensity in an adjacent spectral region (i.e. continuum) in which there is no Fraunhofer absorption line.

In their simpliest form, these Fraunhofer line discriminator systems employ a narrow band filter tuned to pass a selected known Fraunhofer absorption line; a means to detect the intensity of reflected light within the selected Fraunhofer line; and means to detect the intensity of reflected light just outside the selected Fraunhofer line. The measured intensities are then applied to a well established, relationship to determine the intensity of the luminescence and reflectance of the measured material. For a more detailed description of these known Fraunhofer line discriminator systems and their operations, see U.S. Pat. Nos. 3,578,848; 3,598,994; 3,641,344; 3,769,516; and 4,433,245. While these known prior art systems provide measurements of luminescence, their design (especially that of large optical assemblies involved) has restricted their use to permanent installations, e.g. laboratories, or to large mobile units such as aircraft or satellites.

In co-pending U.S. patent application No. 509,681, filed June 30, 1983, and commonly assigned to the present assignee, a luminescence sensing and measuring apparatus (i.e. radiometer) is disclosed which utilizes a novel, simplified optical filter assembly which allows the apparatus to be of lightweight construction and highly portable thereby overcoming the use restrictions of the prior art systems. This lightweight optical filter assembly allows the apparatus to be hand carried into the field for measuring luminescence of target materials on site. To meet the desired lightweight requirement and still be functional over a wide range of Fraunhofer lines of possible interest, the elements of the primary optical filter assembly of the above-mentioned radiometer are mounted on a base element which, in turn is readily positioned into and removed from the radiometer during field operation. By having an individual optical filter assembly designed especially to sense the luminescence related to each of the specific Fraunhofer lines of interest, a particular assembly can be quickly interchanged into the radiometer to sense the luminescence about that particular Fraunhofer line.

More specifically, the lightweight optical assembly of the above-mentioned radiometer is comprised of three filter elements which are affixed in a defined relationship onto a base plate. The first filter is a beamsplitting element whose filter characteristics are centered upon the Fraunhofer line of interest and has a wide bandpass. The first filter is positioned to lie in the line of sight with the light reflected from the material to be investigated when the filter assembly is in position in the radiometer. The combined visible reflected light and the light due to luminescense from the material is directed onto and is split by the first beamsplitter filter. Approximately fifty percent of this light passes through the first beamsplitter filter and continues through the second of the filter elements which, in turn, is centered on the selected Fraunhofer line and which has a narrow passband width (e.g. 4 Angstroms). The light beam passing through the second filter is focused by a lens system onto a first sensor which measures the intensity of said light beam. This measurement is representative of the intensity of light within the Fraunhofer line.

The redirected light beam from the first beamsplitter filter is passed onto the third filter element of the optical assembly which is actually a second beamsplitter. The third filter is centered on the selected Fraunhofer line and has a wide pass band (e.g. 100 Angstroms). Approximately, fifty percent of the light passes through the third filter and is focused via a light gathering lens system onto a second sensor where the intensity thereof is measured. This measurement is representative of the intensity of light in the continuum just outside the Fraunhofer line. The redirected light beam from the third filter (i.e. second beamsplitter) is passed to a eyepiece through which the radiometer is sighted onto the material to be investigated.

While the optical assembly of this previous radiometer is simple and compact, two beamsplitters are used to establish the desired optical paths through the radiometer. As will be understood by those skilled in the art, when light passes through a solid-state beamsplitter of the type involved in the above-mentioned radiometer, it undergoes a certain amount of polarization due to the dielectric properties of the glass used in such beamsplitters. The polarization effects, which are quasi-random, result in amplitude distortions which may adversely affect the measurements at both the first and second sensors. Further, since the beam of light to the second sensor actually passes through two solid-state beamsplitters, the amplitude distortion observed at the second sensor is not the same as that observed at the first sensor which may lead to an undesired inbalance between sensors and thereby affect their measurements. That is, if the light energy reading at the first sensor is not matched to that of the second sensor, when there is no luminescence emanating from the target, then there will inherently be an error when luminescence readings are taken.

Therefore, it can be seen that the repeatability of these measurements can be improved by alleviating the adverse polarization of the light beams being measured and by better optically aligning and balancing the light channels for the sensors.

DISCLOSURE OF THE INVENTION

The present invention provides a radiometer for detecting luminescense from a material (i.e. target) which includes an interchangeable optical assembly of lightweight construction which substantially alleviates the adverse polarization effects normally experienced in radiometers of this type and which further provides an improved balance and optical alignment between the light beams being sensed by the radiometer.

More specifically, the radiometer of the present invention comprises a housing having a aperture through which a light beam from the target enters the radiometer. An optical filter assembly is removably mounted in the housing and is designed to sense certain values of luminescense and reflectance related to a particular Fraunhofer absorption line which is present in the reflected light contained in the light beam from the target. As will be understood, a particular optical assembly is removed and replaced with a different particular Fraunhofer line optical assembly when a measurement is to be made of material from which light is reflected having the different particular Fraunhofer line.

The optical filter assembly of the present invention is comprised of a base plate which can be readily positioned in and removed from the housing of the radiometer. A single beamsplitter and two filter means are mounted on the base plate. The beamsplitter is carried by a mount which adjustable about both a vertical and horizontal axis so that it can be fine-tuned for accuracy. Both filter means are carried by mounts which are adjustable about a vertical axis so that they, too, can be accurately aligned before measurements are taken.

The light beam from the target enters the aperture in the housing and is first filtered by a broad bandwidth filter to pass only visible spectrum light to the beamsplitter. The single beamsplitter which forms an important part of the present invention is comprised of a clear glass reticle that has had a large portion of its surface are a "silvered" to provide a mirrored surface for reflecting and redirecting a fraction (i.e. second fraction) of the visible light beam from the target. A first fraction of the visible light beam passes through the clear portion of the beamsplitter and on through a first filter means carried by a first of the adjustable filter mounts on the base plate.

The first filter means is filter element which is optically centered on the particular Fraunhofer line and having a broad bandwidth frequency (e.g. 100 Amstroms) which passes only substantially the reflected light in the two continuums adjacent (i.e. just outside) the particular Fraunhofer line. This light is focused by a lens system onto a first sensor in the housing which measures its intensity and generates a signal representative thereof.

The second fraction of the light beam which is reflected by the beamsplitter passes through a second filter means which is carried by the other filter mount on the base plate. The second filter means has a blocking filter element which eliminates the multiple transimission bands in the second fraction of the light beam and a narrow bandwidth frequency filter element (e.g. 4 Angstroms) centered at the particular Fraunhofer line which passes only substantially the light at the particular Fraunhofer line. This light is focused onto a second sensor in the housing which measures the intensity thereof and generates a representative signal. As will be understood by those skilled in the art, these signals can then be processed to calculate the luminescense and reflectance emanating from the target.

The optical filter assembly also includes a fourth adjustable mount which carries a reflecting means and which can be moved into and out of the path of the first fraction of the light beam after it passes through the beamsplitter. When the reflecting means is in the path of the first fraction, it reflects the first fraction of the light beam to an eyepiece in the housing whereby the radiometer can be visually sighted on the target and precisely aligned both geometrically and optically to the center of the target material.

Since the light (i.e. first fraction) passing through the clear portion of the beamsplitter experience more polorization than that reflected therefrom, as much of beamsplitter's surface area as is practical will be mirrored so that the majority of the light beam will be reflected and hence, will not experience any substantial polarization. Further, since the majority of the light beam (e.g., as much as 90%) is reflected to the narrow bandwidth filter while the remaining light (e.g. 10%) is passed to the broad bandwidth filter, the light beams sensed at the first and second sensors can be substantially balanced by proper design of the beamsplitter and polorization is minimized in the two channels.

BRIEF DESCRIPTION OF THE DRAWINGS

The actual construction, operation, and apparent advantages of the present invention will be better understood by referring to the drawings in which like numerals identify like parts and in which.

BEST MODE FOR CARRYING OUT THE INVENTION

Figure 1A:
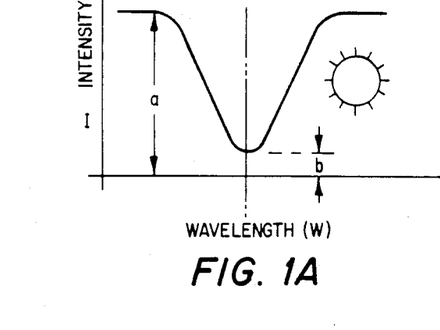
FIG. 1A and 1B are idealized graphic illustrations of the relationship of a Fraunhofer line present in the sun and the narrow "C" channel characteristics and their relationships which are used to calculate luminescense.
Figure 1B:
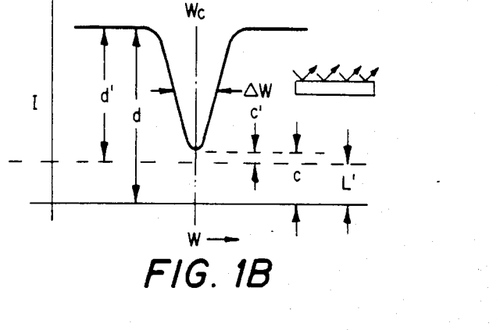

In order to better appreciate the present invention, a brief discussion of known luminescense phenomena will be set forth before the details of the invention are described. FIG. 1A is a idealized graphical illustration of light intensity (I) of direct sunlight over a portion of the spectrum which includes a particular Fraunhofer line $w_c$ over an average bandwidth $\Delta^2 w$. While a particular Fraunhofer line is usually referred to as a single number, e.g. 5890 angstroms. This number represents the center wave length of the Fraunhofer line which encompass a narrow bandwidth. FIG. 1B is a graphical representation of light intensity (I) of reflected sunlight plus any luminescence (L) from a target (e.g. a material under investigation). In FIGS. 1A and 1B:

a = light intensity in the continuum adjacent a selected Fraunhofer line ($w_c$) for a direct sunlight sky scene;

b = light intensity in a narrow spectral band centered at the Fraunhofer line ($w_c$) for said sky scene;

c = light intensity in a narrow spectral band centered at the Fraunhofer line ($w_c$) which emanates from the material under investigation (target); and d = light intensity in the continuum adjacent the Fraunhofer line ($w_c$) which emanates from the target.

The following relationships can be established referring to FIGS. 1A and 1B:

d'/a = c'/b = R (Reflection Coefficient)
L'/a = L (Luminescense Coefficient)
c = c' + L' and d = d' + L'

Then:
c = Rb + La
d = Ra + La

Solving these two equations simultaneously gives:
R = [(d−c)/(a−b)] and
L = [d/a] − [(d−c)/(a−b)] = [d/a] − R It has been found, however, that the ratio b/a is a very convenient system parameter and can be determined without direct measurement of the values of a and b. However, a measurement has to be made to represent the scaling factor "a" in the above relationship. This measurement is made using a fairly broad band instrument looking vertically into the sky scene. Therefore, the expression for luminescenses (L) can be simplified as follows:

$$L = [d/a] \, [((c/d) - n)/(1 - n)] \text{ or}$$

$$L = \frac{1}{a(1-n)} [c - nd] \text{ wherein:}$$

$$n = \frac{b}{a}$$

Figure 2:
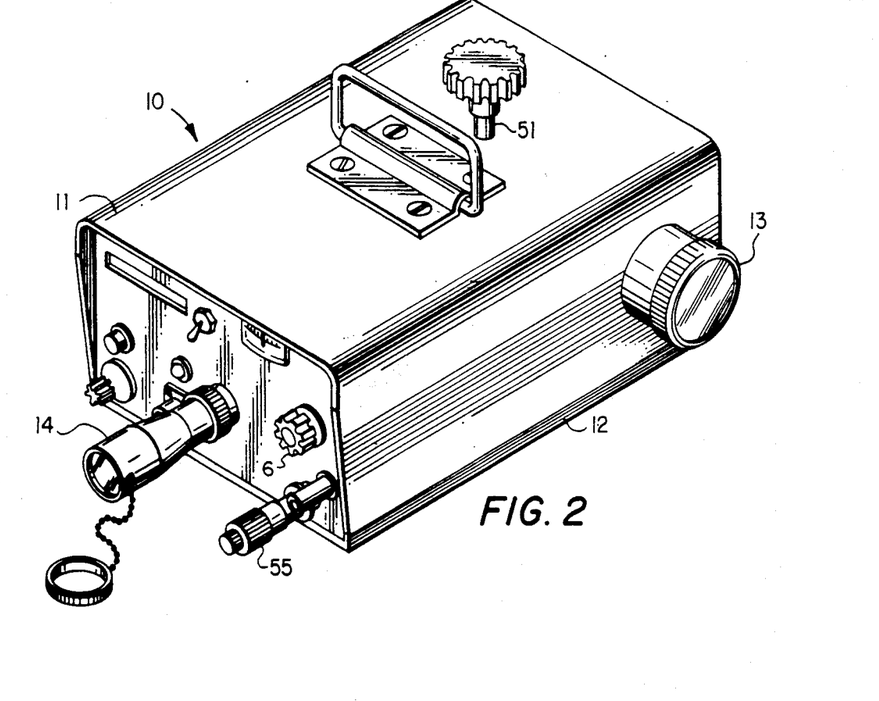
FIG. 2 is a perspective view of a typical external configuration of a radiometer in accordance with the present invention.

The present invention provides a lightweight and highly portable apparatus for actually measuring the c and d intensities of light emanating from a target material which are then used in the above expression to arrive at the luminescense component emanating from the target material. More particularly, FIG. 2 illustrates a typical external configuration of luminescense sensing means 10, hereinafter called a "radiometer". Radiometer 10 is comprised of a housing 11 having a box-like case which is removably mounted on a base 12.

Housing 11 has a target aperture 13 through the side thereof. A viewfinder eyepiece 14 extends through front panel 6 of the radiometer 10 for a purpose that will become obvious below. Various other switches and controls are positioned through and on front panel 6 and top of housing 11 and will be discussed at the appropriate times during the following description.

Figures 3, 5:
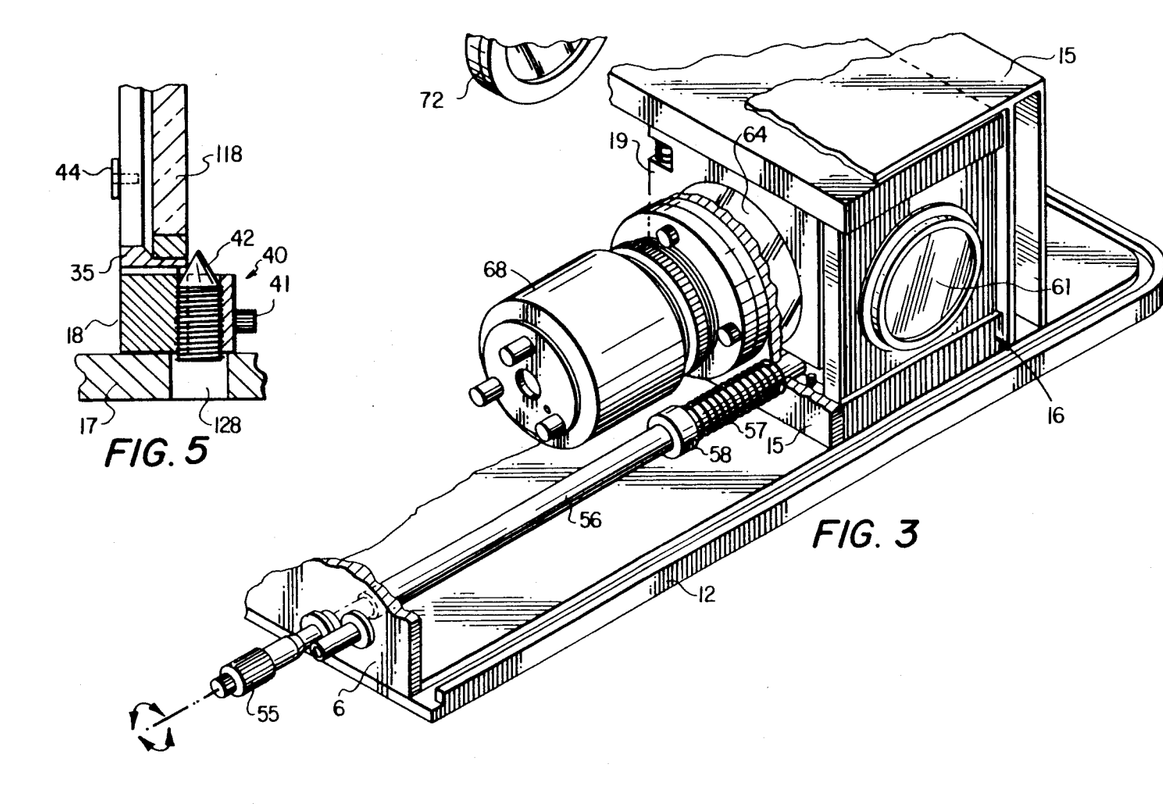
FIG. 3 is a cutway view of a portion of the internal structure of the radiometer of FIG. 1.
FIG. 5 is a sectional view taken along line 5—5 of FIG. 4.
Figure 4:
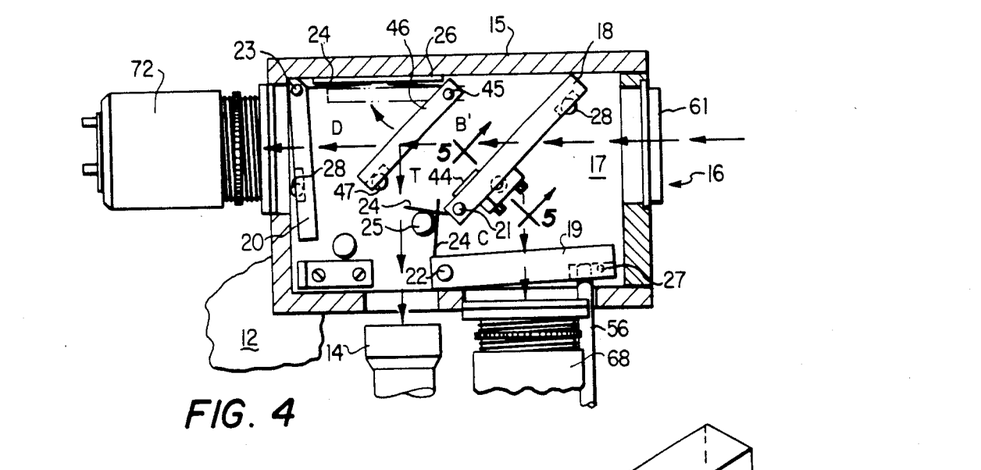
FIG. 4 is a top view of the optical assembly of the present invention in place in the radiometer.
Figure 6:
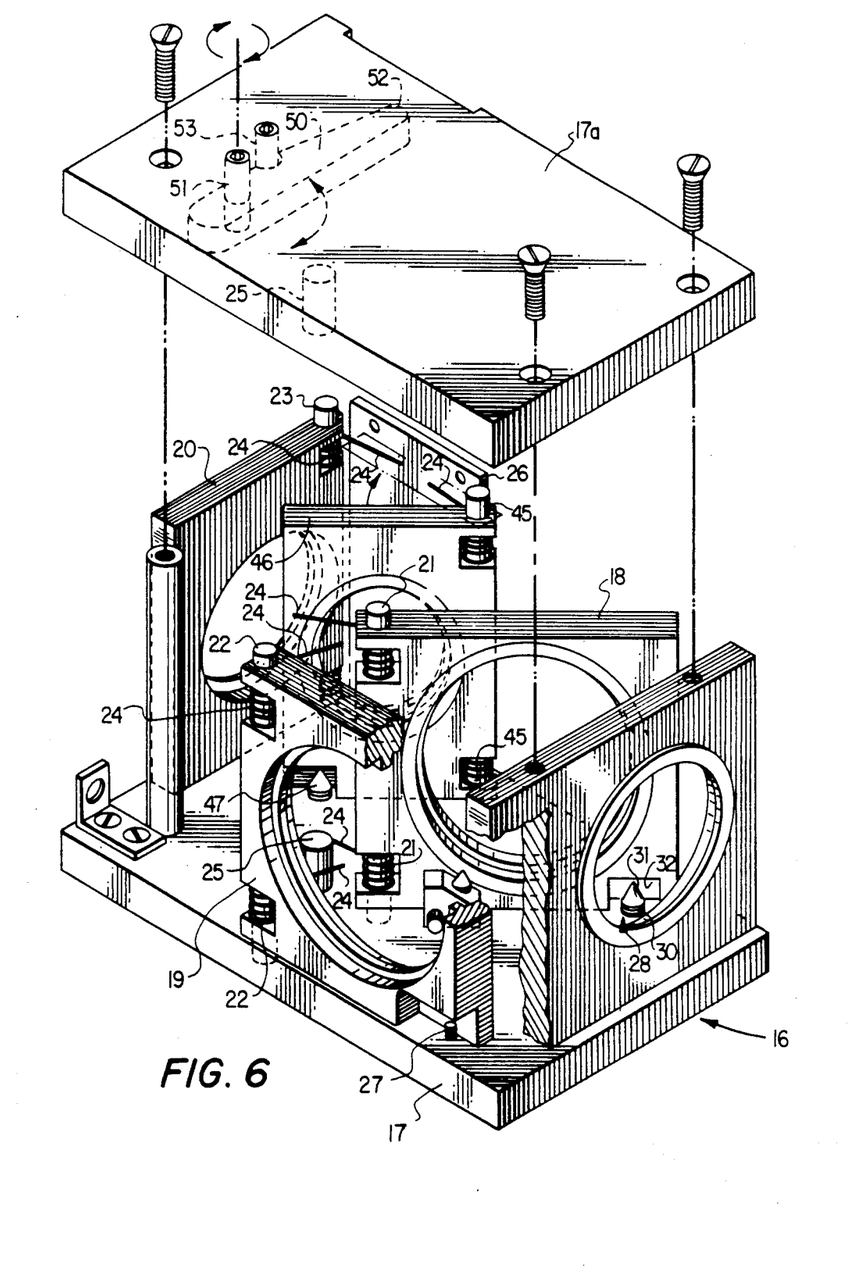
FIG. 6 is an exploded, perspective view, partly in section, of the mechanical elements of the present optical filter assembly.

Referring now to FIGS. 3 and 4, a compartment 15 (shown partly broken away) is provided on base 12 into which optical filter assembly 16 is removably positioned. As seen in FIGS. 4–7, optical filter assembly 16 is comprised of a base plate 17 having a beamsplitter mount 18 and two filter element mounts 19 and 20, all pivotably mounted between base plate 17 and upper plate 17a by vertical pivot pins 21, 22 and 23, respectively, for rotational movement about a vertical axis. Torsional springs 24 encompass respective pins 21, 22 and 23 and have ends that bear against stops (e.g. stub posts 25, plate 26 respectively) to bias said mounts in a first rotational direction. Mount 19 is braced against stop 27 while mounts 18 and 20 are braced against adjustable stops 28. Adjustable stops 28 are of the same basic construction and each is comprised of a screw 30 which is threaded upward through plate 17 and which has a conical upper end or tip 31 which cooperates with a complementary tapered surface 32 on the respective mount 18, 20 (see FIGS. 6 and 7). It can be seen that conical tip 31 will bear against surface 32 as screw 30 is threaded upward to cam (i.e. rotate) its respective mount against the bias of springs 24 to angularly align said mount about its respective vertical axis.

Figure 7:
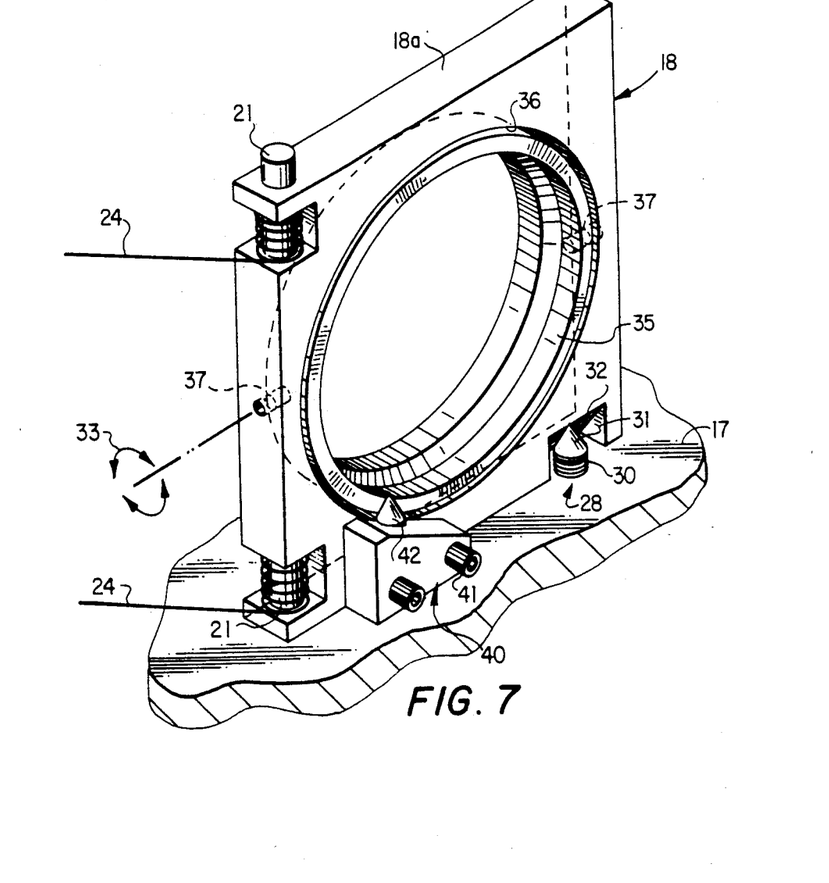
FIG. 7 is a perspective view of the beamsplitter mount of the present invention.

While filter mounts 19 and 20 are similar in construction, due to the function to be performed by the beamsplitter, a more universal adjustment is desired of beamsplitter mount 18. As seen in FIGS. 5 and 7, a retainer ring 35 is pivoted mounted within a horizontal opening 36 through support 18a of mount 18 by pins 37 for rotational movement about a horizontal axis 33. Adjustment means 40 is mounted on support 18a by screws 41 or the like and has a conically-tipped screw 42 threaded therethrough. The conical surface of screw 42 cooperates with the lower edge of ring 35 to rotate same about pins 37 and against the bias of a leaf spring 44 or the like (FIG. 4) which, in turn, is affixed to mount 18 on the side opposite adjustment means 40.

Also pivotably mounted on plate 17 by pivot pins 45 is mirror mount 46. Springs 24 which engage plate 26 normally biases mount 46 out against adjustable stop 47 which is of the same construction as that of stops 28 described above. Mirror mount 46 is mounted to be rotated about pins 45 into the optical path of a light beam passing through optical assembly 16 as will be explained in detail below. To rotate mount 46, a cam 50 (FIG. 6) is releasably connected to a shaft 51 which extends through upper plate 17 and through housing 11 (FIG. 2). The outer edge 52 of cam 50 abuts the surface of mount 46 which faces mount 18. When cam 50 is against stop 53, mirror mount 46 is pushed to its retracted or stowed position (dotted lines in FIG. 4). When cam 50 is moved against stop 25, mount 46 is biased by spring 24 into engagement with adjustable stop 47 (FIG. 4). The purpose for moving mirror mount 46 between its two positions will become obvious from the discussion of operation set forth below.

The heads of all the screws of the adjustable means 28, 40 and 47 are accessible from the underside of housing 11 through openings 128 (only one shown in FIG. 5) in base plate 17 of optical assembly 16 which align with complementary openings (not shown) in base 12 when optical assembly 16 is in an operable position within housing 11. A removable cover plate (not shown) is positioned over the complimentary openings when not in use to block entry of any extraneous light into the housing. A tool, e.g. allen-head wrench can be inserted through the aligned openings to rotate a particular screw of an adjustment means to fine-tune the beamsplitter mount 18 (both vertically and horizontally), filter mount 20, and mirror mount 46 to accurately align the components.

It will be understood that optical assembly 16 as described above is easily placed and removed from compartment 15 on base 12. By being able to replace the optical filter assembly 16 within radiometer 10, an individual assembly 16 can be designed and constructed for each individual Fraunhofer line of interest so that materials having luminescense at different Fraunhofer lines can be examined in the field by merely exchanging the appropriate optical filter assemblies 16.

Now that the mechanical details of optical filter assembly 16 have been described, the optical details of radiometer 10 will now be set forth. This may be best understood by referring to FIG. 8 which schematically illustrates the pathes that the various light beams take through radiometer 10. First, radiometer 10 is sighted onto target 60 (e.g. material from which luminescense is to be measured). This is done by rotating shaft 51 (FIGS. 1 and 6) to move a reflecting mirror 146 carried by mirror mount 46 to the operable position shown in FIG. 8. As can been seen from FIG. 8, light from target 60 will pass through beamsplitter 118 carried by retainer ring 35 in mount 18 and will be reflected by mirror 146 into eyepiece 14. Once radiometer 10 is properly sighted on the target, mirror 146 is retracted to its stowed position (dotted lines in FIG. 8).

Figure 8:
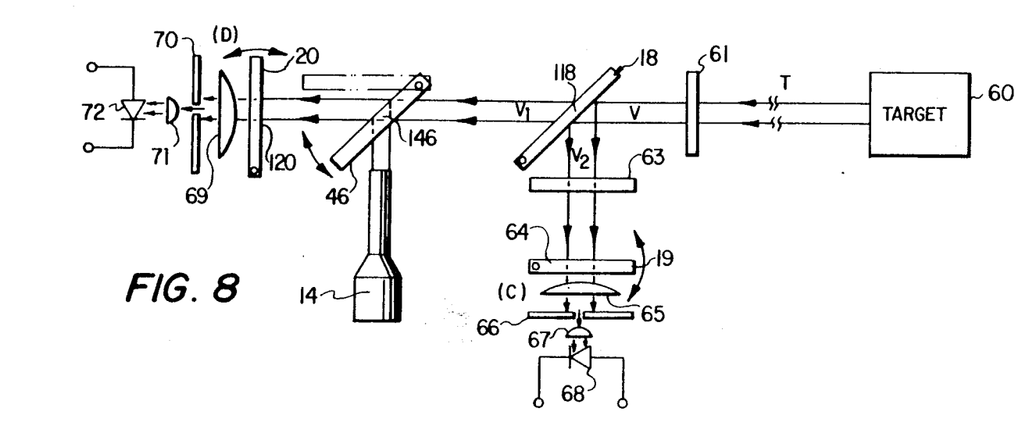
FIG. 8 is a schematical view of the optical filter assembly of the present invention of the present invention and the respective light paths therethrough.

Light T from target 60 (both reflected light and light due to luminiscense) enters radiometer 10 through target aperture 13 and passes through a broad bandwidth filter 61 (e.g. 3000–8000 angstroms) to produce a light beam V which is limited to the visible and spectrum light T from the target. Light beam V then impinges upon beamsplitter 118.

A first fraction $V_1$ of light beam V passes directly through beamsplitter 118 (which will be described in further detail below) and then passes through filter 120 which is carried by filter mount 20. Filter 120 has a broad bandwidth (full width half maximum) of 100 Angstroms centered on the selected Fraunhofer line of interest. The light beam D from filter 120 next passes through lens 69, field stop 70, condensing lens 71, and onto photodiode 72, which measures the intensity of D. This measurement is representative to the "d" component or factor needed to calculate the luminescense and reflectance from target 60.

A second fraction $V_2$ of light beam V is reflected and redirected from the angular positioned beamsplitter 118. The second fraction $V_2$ passes through blocking filter 63 which has a nominal bandwidth (full width half maximum) of 100 Angstroms centered on the selected Fraunhofer line. Filter 63 serves to eliminate the unwanted multiple transmission bands which would otherwise increase the apparent energy (i.e. intensity) reading at the Fraunhofer line frequency.

Light passing through filter 63 continues through narrow bandwidth filter 64. Filter 64 is a tuneable filter having a narrow bandwidth frequency of 4 angstroms (i.e. full width, half maximum bandwidth) which is centered on the selected Fraunhofer line. It should be understood that both Filters 63 and 64 can both be mounted in mount 19 or their optical functions can be combined into a single unit such as filter units fabricated by Barr Associates of Massachussetts.

As seen in FIG. 3, filter mount 19 and hence, narrow bandwidth filter 64 can be fine-tuned on site by means of rod 56 which extends through compartment 15 and into contact with the face of mount 19. Rod 56 is threaded or simularly positioned through the front panel 6. A spring 57 is positioned between compartment 15 and a stop ring 58 affixed on rod 56 to normally bias rod 56 away from mount 19. It can be seen that by rotating knob 55 on rod 56 to thread same into the housing, mount 19 will be rotated about is vertical axis by the rod to fine-tune and properly angularly align filter 64.

The light beam C passing through narrow bandwidth filter 64 next passes through an lens 65, a field stop 66, condensing lens 67, and onto photodiode 68 which measures the intensity of C which represents the "c" component of the luminescense and reflectance equations set forth above.

Photodiodes 68 and 72 are blue-enhanced photovoltaic devices, e.g. model SD-200-12-12-241, distributed by Silicon Detector Corporation, which produce signals representative of the measured intensities and which can be stored or supplied directly to a processing means (not shown) for determining the luminescense and reflectance emanating from the target 60.

As mentioned above, solid-state beamsplitters such as those used in known prior art radiometers produce adverse polarization effects on both light passed therethrough and especially from light reflected therefrom. Beamsplitter 118 of the present invention is so constructed that polarization of both the reflected light beam and passed light beam is substantially alleviated.

Figure 9:
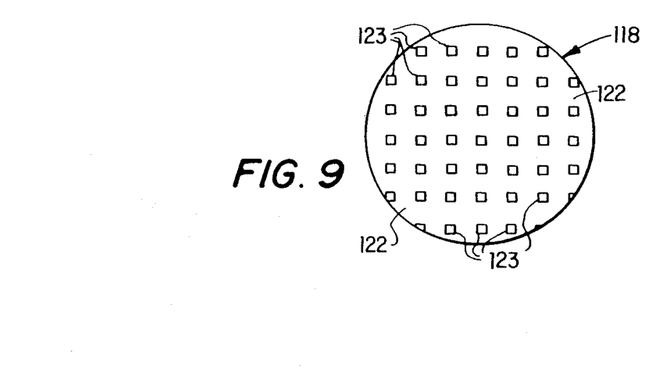
FIG. 9 is a front view of a preferred beamsplitter of the present invention.

More specifically, beamsplitter 118 (9) is comprised of a clear glass reticle 122 having low dielectric properties. A predetermined portion of the surface area of reticle 122 is "silvered" to form a mirrored, reflecting surface area on reticle 122. The reticle is silvered on its front face as opposed to the back thereof to eliminate possible reflectance off the glass (i.e. front face) which would otherwise overlie the mirrored areas. The term "silvered" as used herein is meant to mean silver, nichrome, aluminum, gold, or equivalent reflective materials. The higher the reflective coefficient of the deposited surfaces, the less polarization will be present in the "c" channel light. The fraction of the total surface area of reticle 122 that is mirrored is proportional to the second fraction $V_2$ of the light beam V which is to be reflected. That is, if 90% of V is to be reflected, a total of 90% of the surface area of reticle 119 will be mirrored.

As a practical matter, the ratio of beam width of D to C allows a very high ratio of mirrored-surfaced area to clear area. However, the ratio is limited in the configuration shown in FIG. 8 by the amount of light $V_1$ that is required for use of eyepiece 14 when mirror 146 is in the light path. It should be understood, that this ratio can be increased if mirror 146 is repositioned (not shown) to be movable into and out of the path of the majority light beam $V_2$.

The actual configuration of the mirrored area in relation to the clear area of reticle 122 is not critical as long as their respective total areas area in the desired ratio. FIG. 9 discloses a preferred configuration for beamsplitter 118 wherein a plurality of rows of spaced silvered squares or dots 123 are affixed on reticle 122.

With the beamsplitter 118, only the light $V_1$ that passes through the clear portion of the beam-splitter experiences any substantial polarization. Since the light $V_2$ is reflected from a highly reflective metallic (poor dielectric) surface, it experiences very litte adverse polarization effects. Further, since the majority of the light beam V is reflected by the beamsplitter (as will be explained more fully below), and only a small fraction of light passes therethrough, the present optical filter assembly substantially alleviates the total polarization effects in both the C and D channels.

In order to accurately measure luminescense and reflectance, ideally the values measured from the C and D channels should be exactly equal to each other when readings are taken from a target having no luminescense. In other words, the C and D channels must be balanced (as close as is practically possible) to obtain meaningful readings of luminescense. To do this in the present invention, the fraction $V_1$ of light V going to filter 64 having a broad bandwidth W, is proported to the fraction $V_2$ going to filter 64 having a narrow bandwidth $W_2$ in accordance with the following simple relationship:

$$V_1 W_1 = V_2 W_2$$

Since the bandwidth of filter 64 is always substantially less than that of filter 120, the majority of the light will always be reflected with very little polarization and only the small fraction $V_2$ which passes through the clear portion of beamsplitter 118 will undergo a somewhat higher polarization. The C and D channels are substantially balanced for a particular Fraunhofer line optical filter assembly 16 by providing a beamsplitter 118 having the desired mirrored to clear surface area which is checked at zero luminescense. The final balance between the C and D channels can be fine-tuned by known electronic and/or optical means, e.g. sharply focusing the light beams at C and D sensors through their respective field stops 66 and 70.

What is claimed is:

1. A radiometer for detecting certain components of luminescense and reflected light contained in a light beam from a target wherein the reflected light in said light beam includes a particular Fraunhofer line, said radiometer comprising:
   a housing having an aperture therein for receiving said light beam from said target;
   an optical filter assembly in said housing comprising:
   a beamsplitter positioned directly in the path of said light beam, the surface of said beamsplitter having a clear portion for passing a first fraction of said light beam through said beamsplitter and a mirrored portion for reflecting and redirecting the remaining second fraction of said light beam from said beamsplitter;
   a first filter means positioned directly in the path of said first fraction of said light beam, said first filter means being optically centered on said particular Fraunhofer line and having a broad bandwidth frequency which passes only substantially the light in the continuums adjacent Fraunhofer line; and
   a second filter means positioned directly in the path of said second fraction of said light beam, said second filter means being optically centered on said particular Fraunhofer line and having a narrow bandwidth frequency which passes only the light at said particular Fraunhofer line;
   a first sensor means in said housing for sensing said light passing through said first filter means and generating a signal representative of the intensity thereof; and
   a second sensor means in said housing for sensing said light passing through said second filter means and generating a signal representative of the intensity thereof.

2. The radiometer of claim 1 wherein said mirrored portion of said beamsplitter's surface area is larger than said clear portion of said surface area whereby a majority of said light beam is reflected and redirected by said beamsplitter.

3. The radiometer of claim 2 wherein said beamsplitter comprises:
   a clear glass reticle having a front face; and
   a plurality of rows of spaced, mirrored areas positioned and affixed on the front face of said clear glass reticle.

4. The radiometer of claim 2 including:
   an eyepiece in said housing; and
   wherein said optical filter assembly includes:
   a reflecting means; and
   means to move said reflecting means into and out of the path of said first fraction of said light beam after it has passed through said beamsplitter whereby said first fraction of light will be reflected to said eyepiece when said reflecting means is moved into the path of said first fraction of said light beam.

5. The radiometer of claim 3 wherein said narrow bandwidth frequency of said second filter means is equal to approximately 4 angstroms and said broad bandwidth frequency of said first filter means is equal to approximately 100 angstroms.

6. The radiometer of claim 5 wherein said second filter means further includes:
   a blocking filter element to eliminate multiple transmission bands in said second fraction of said light beam.

7. The radiometer of claim 6 including: filter means in said housing aligned with said aperture and directly in the path of said light beam from said target, said filter means having a bandwidth frequency for passing only the visible spectrum light beam from the target.

8. The radiometer of claim 7 wherein said optical filter assembly further comprises:
   a base plate removably positioned in said housing and having said beamsplitter, said first filter means, said second filter means, and said reflecting means all mounted thereon.

9. The radiometer of claim 8 including:
   means for adjusting the alignments of said beamsplitting, said first filter means, and said second filter means on said base plate.

10. An optical filter assembly for a radiometer to be used for detecting and measuring certain components of luminescense and reflected light contained in a light beam from a target wherein said reflected light includes a particular Fraunhofer line, said optical filter assembly comprising:
    a base plate adapted to be removably positioned in said radiometer;
    a beamsplitter mount on said base plate and positioned to lie directly in the path of said light beam which said base plate is in an operable position in said radiometer;
    a beamsplitter carried by said beamsplitter mount, the surface of said beamsplitter having a clear portion for passing a first fraction of said light beam through said beamsplitter and a mirrored portion for reflecting and redirecting the remaining second fraction of said light beam from said beamsplitter;
    a first filter mount on said base plate and positioned to lie directly in the path of said first fraction of said light beam when said base plate is in a operable position in said radiometer;
    a first filter means carried by said first filter mount, said first filter means being optically centered on said particular Fraunhofer line and having broad bandwidth frequency which passes only substantially the light in the continuums adjacent said Fraunhofer line;

a second filter mount on said base plate and positioned to lie directly in the path of said second fraction of said light beam when said base plate is in an operable position in said radiometer, and a second filter means carried by said second filter mount, said second filter means being optically centered on said particular Fraunhofer line and having a narrow bandwidth frequency which passes only the light at said particular Fraunhofer line;

11. The optical filter assembly of claim 10 wherein said mirrored portion of said beamsplitter's surface area is larger than said clear portion of said surface area whereby a majority of said light beam will be reflected and redirected by said beamsplitter.

12. The optical filter assembly of claim 11 wherein said beamsplitter comprises:

a clear glass reticle; and a plurality of rows of spaced, mirrored areas positioned and affixed on said clear glass reticle.

13. The optical filter assembly of claim 11 including:

a fourth mount pivotably mounted on said base plate intermediate said beamspliter and said second mount, a reflecting means carried by said fourth mount; and means to move said fourth mount into and out of the path of said first fraction of said light beam after first fraction has passed through said beamsplitter, said reflecting means adapted to reflect and redirect said first fraction when said fourth mount is moved into the path of said first fraction.

14. The optical filter assembly of claim 13 wherein said narrow bandwidth frequency of said second filter means is equal to approximately 4 Angstroms and said broad bandwidth frequency of said first filter means is equal to approximately 100 Angstroms.

15. The optical filter assembly of claim 14 wherein said second filter means further includes:

a blocking filter element to eliminate multiple transmission bands in said second fraction of said light beam.

16. The optical filter assembly of claim 10 including:

means for pivotably mounting said beamsplitter mount on said base plate for rotation about a vertical axis, and means for adjusting the position of said beamsplitter mount about said vertical axis.

17. The optical filter assembly of claim 16 including:

means for pivotably mounting said first filter mount on said base plate for rotation about a vertical axis;

means for adjusting said first filter mount about its said vertical axis;

means for pivotably mounting said second filter mount on said base plate for rotation about a vertical axis; and means for adjusting said second filter mount about its said vertical axis.

18. The optical filter assembly of claim 17 wherein said beamsplitter mount comprises:

a support pivotably mounted on said base plate for rotational movement about a vertical axis, said support having a horizontal opening therethrough;

a retainer ring adapted to carry said beamsplitter;

means to pivotably mount said retainer ring within said opening for rotational movement about a horizontal axis therein; and means for adjusting said retainer ring about said horizontal axis.

19. The optical filter assembly of claim 18 wherein said means for adjusting said beamsplitter mount about its vertical axis comprises:

means to bias said support in a first direction about said vertical axis; and a screw threaded through said base plate and having a conical tip in contact with a tapered surface on said support whereby said conical tip and said tapered surface cooperate to move said support against said bias means as said screw is threaded into said base and said bias means move said support in said first direction as said screw is threaded out of base plate.

20. The optical assembly of claim 19 wherein said means for adjusting said retainer ring about its horizontal axis comprises:

means to bias said ring in a first direction;

a screw threaded on said support and having a conical tip in contact with said ring whereby said ring is moved by said conical tip against said bias means when said screw is threaded upwardly in said support and said bias means moves said ring in said first direction when said screw is threaded downwardly in said support.

* * * * *

UNITED STATES PATENT OFFICE
CERTIFICATE OF CORRECTION

PATENT NO. : 4,671,662
DATED : June 9, 1987
INVENTOR(S) : Joseph E. Zupanick et al.

It is certified that error appears in the above-identified patent and that said Letters Patent are hereby corrected as shown below:

Column 10, line 40, "ting," should read --er,--.

Column 10, line 52, "which" should read --when--.

Signed and Sealed this

Twenty-ninth Day of December, 1987

*Attest:*

DONALD J. QUIGG

*Attesting Officer*  *Commissioner of Patents and Trademarks*